(12) United States Patent
Humayun et al.

(10) Patent No.: US 9,919,140 B2
(45) Date of Patent: Mar. 20, 2018

(54) IMPLANTABLE OXYGENATOR WITH SELF-CONTAINED ELECTROLYTE

(71) Applicants: UNIVERSITY OF SOUTHERN CALIFORNIA, Los Angeles, CA (US); DOHENY EYE INSTITUTE, Los Angeles, CA (US); CALIFORNIA INSTITUTE OF TECHNOLOGY, Pasadena, CA (US)

(72) Inventors: Mark S. Humayun, Glendale, CA (US); Karthik Murali, Los Angeles, CA (US); Ramiro Magalhaes Ribeiro, South Pasadena, CA (US); Yu-chong Tai, Pasadena, CA (US); Nicholas Scianmarello, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 166 days.

(21) Appl. No.: 14/433,583

(22) PCT Filed: Oct. 7, 2013

(86) PCT No.: PCT/US2013/063720
§ 371 (c)(1),
(2) Date: Apr. 3, 2015

(87) PCT Pub. No.: WO2014/055989
PCT Pub. Date: Apr. 10, 2014

(65) Prior Publication Data
US 2015/0273197 A1    Oct. 1, 2015

Related U.S. Application Data

(60) Provisional application No. 61/710,233, filed on Oct. 5, 2012.

(51) Int. Cl.
*A61M 37/00* (2006.01)
*A61F 9/00* (2006.01)
(Continued)

(52) U.S. Cl.
CPC ........... *A61M 37/00* (2013.01); *A61F 9/0017* (2013.01); *A61M 5/14276* (2013.01); *C25B 1/02* (2013.01);
(Continued)

(58) Field of Classification Search
CPC ...... A61M 5/14276; A61M 2210/0612; A61M 2205/3507; A61F 9/0017; A61F 2250/0068; A61N 1/36046; A61N 1/0543
See application file for complete search history.

(56) References Cited

U.S. PATENT DOCUMENTS 6,368,592 B1  4/2002  Colton et al.
8,209,024 B2  6/2012  Greenbaum et al.
(Continued)

FOREIGN PATENT DOCUMENTS

CN    102202618 A    9/2011
CN    104936564 A    9/2015
(Continued)

OTHER PUBLICATIONS

Human eye. (Apr. 2, 2017). In Wikipedia, The Free Encyclopedia. Retrieved 18:48, Apr. 4, 2017, from https://en.wikipedia.org/w/index.php?title=Human_eye&oldid=773408263.*
(Continued)

*Primary Examiner* — Emily Schmidt
(74) *Attorney, Agent, or Firm* — McDermott Will & Emery (57) ABSTRACT

An implantable oxygenator may have a configuration that is suitable for implantation within a human body be implanted within a human body, such as within a human eye. The
(Continued)

implantable oxygenator may include an electrolyte reservoir having a configuration suitable for storing electrolyte and an electrolysis system having a configuration that performs electrolysis on a portion of the electrolyte, thereby producing oxygen in the region of the electrolysis system.

20 Claims, 8 Drawing Sheets

(51) Int. Cl.
    *C25B 1/02*     (2006.01)
    *C25B 9/08*     (2006.01)
    *A61M 5/142*     (2006.01)

(52) U.S. Cl.
    CPC ..... *C25B 9/08* (2013.01); *A61M 2005/14204* (2013.01); *A61M 2205/3334* (2013.01); *A61M 2210/0612* (2013.01)

(56) References Cited

U.S. PATENT DOCUMENTS

| | | | |
|---|---|---|---|
| 2004/0186533 A1 | 9/2004 | Greenberg et al. | |
| 2007/0049987 A1* | 3/2007 | Greenberg | A61F 9/08 607/54 |
| 2008/0039792 A1* | 2/2008 | Meng | A61K 9/0024 604/114 |
| 2008/0046028 A1* | 2/2008 | Franklin | A61N 1/0551 607/53 |
| 2009/0306585 A1 | 12/2009 | Pang et al. | |
| 2009/0306594 A1* | 12/2009 | Pang | A61F 9/00781 604/133 |
| 2010/0168646 A1* | 7/2010 | Greenbaum | A61N 1/20 604/20 |
| 2011/0144617 A1 | 6/2011 | Meng et al. | |
| 2011/0282160 A1* | 11/2011 | Bhadri | A61B 3/0008 600/236 |
| 2011/0295241 A1 | 12/2011 | Ziaie et al. | |
| 2012/0130302 A1 | 5/2012 | Wrobel | |

FOREIGN PATENT DOCUMENTS

| | | |
|---|---|---|
| EP | 2 903 573 | 8/2015 |
| JP | 2010-516398 A | 5/2010 |
| JP | 2011-509120 A | 3/2011 |
| WO | WO01-50983 A1 | 7/2001 |
| WO | WO2006-059322 A2 | 6/2006 |

OTHER PUBLICATIONS

Conjunctiva. (Feb. 11, 2017). In Wikipedia, The Free Encyclopedia. Retrieved 18:51, Apr. 4, 2017, from https://en.wikipedia.org/w/index.php?title=Conjunctiva&oldid=764936562.*

State Intellectual Property Office (SIPO, China). 2016. Office Action dated Apr. 5, 2016 for Chinese Application No. 201380062517.7, entitled "Implantable Oxygenator with Self-Contained Electrolyte," Chinese national phase of PCT WO 2014/055989 (published as CN 104936564 A), counterpart to instant U.S. national phase application.

European Patent Office (EPO). 2016. Extended European Search Report for European Application No. 13843989.8, European regional phase of PCT WP 2014/055989 (published as EP 2 903 573 A0), counterpart to instant U.S. national phase application.

Chinese Office Action dated Dec. 2, 2016, which issued in Chinese Application No. 201380062517.7.

Korean Intellectual Property Office (ISA/KR). 2014. International Search Report and Written Opinion of the International Searching Authority for PCT/US2013/063720, dated Jan. 8, 2014.

Japanese Office Action from Japanese Patent Application No. 2015-535873, dated Aug. 29, 2017, and machine-generated translation, 9 pages.

* cited by examiner

| Retinal Oxygen Consumption Rate (μL/min) | 6.1 |
|---|---|
| 4OH- (aq) --> O2 (g) + 2 H2O(l) + 4e- | |
| Saline Consumption Rate to oxygenate Retina (nL/min) | 7.9 |
| Electron Consumption Rate to oxygenate Retina (nmol/min) | 880.0 |
| Current Consumption Rate to oxygenate Retina (mA) | 1.4 |
| Power Consumption to oxygenate Retina (mW) | 4.2 |
| Saline Consumption to oxygenate Retina (nL/min) | 7.9 |
| Days till next refill, if retina is oxygenated (days) | 8.8 |
| Power Consumption to oxygenate Macula (mW) | 0.1 |
| Saline Consumption to oxygenate Macula (nL/min) | 0.2 |
| Days till next refill, if macula is oxygenated (days) | 350.0 |

IMPLANTABLE OXYGENATOR WITH SELF-CONTAINED ELECTROLYTE

CROSS-REFERENCE TO RELATED APPLICATIONS

This application is a national phase application of PCT Application No. PCT/US2013/063720, which is based upon and claims priority to U.S. provisional patent application 61/710,233, entitled "Novel Oxygen Therapy Treatment for Retinal Ischemia," filed Oct. 5, 2013.

This application is also related to U.S. patent application Ser. No. 12/523,990 (issued Jun. 26, 2012 as U.S. Pat. No. 8,209,024 B2), which is a national phase filing of PCT Application PCT/US08/00742, filed Jan. 22, 2008, both entitled "Method and Apparatus for Treating Ischemic Diseases".

The entire content of all of these applications is incorporated herein by reference.

BACKGROUND

Technical Field

This disclosure relates to implantable oxygenators, including implantable oxygenators that are sized and configured to be implanted in a human eye.

Description of Related Art

Ischemic retinal diseases, such as diabetic retinopathy (DR) and retinal vein occlusions (RVO), are leading causes of blindness. Although DR and RVO have different underlying pathophysiology, the common end-result may be inner retinal ischemia.

Retinal ischemic diseases may be treated with a focal laser, pan-retinal photocoagulation, drug therapy, or vitrectomy. Focal laser, pan-retinal photocoagulation (PRP), and monthly injections of pharmacologic agents may not treat the underlying pathology. Laser treatment can cause side effects like scotoma and late light adaptation. Pars Plana Vitrectomy (PPV) may not supply oxygen to the ischemic retina and can lead to anterior segment neo-vascularization.

SUMMARY

An implantable oxygenator may have a configuration that is suitable for implantation within a human body be implanted within a human body, such as within a human eye. The implantable oxygenator may include an electrolyte reservoir having a configuration suitable for storing electrolyte and an electrolysis system having a configuration that performs electrolysis on a portion of the electrolyte, thereby producing oxygen in the region of the electrolysis system.

The implantable oxygenator may include an internal control system that controls the concentration of oxygen produced by the electrolysis system. The internal control system may wirelessly receive control information indicative of a desired concentration of oxygen to be produced by the electrolysis system and control the concentration of oxygen produced by the electrolysis system in accordance with this received information. The internal control system may include an oxygen sensor that senses the concentration of oxygen produced by the electrolysis system.

The implantable may include an internal control system that controls when oxygen is produced by the electrolysis system. The internal control system may wirelessly receive control information indicative of when oxygen should be produced by the electrolysis system and control the production of oxygen produced by the electrolysis system in accordance with this received information.

The electrolysis system may include an electrolysis compartment that is separate from the electrolyte reservoir. The electrolysis compartment may include electrodes within the electrolysis compartment. A cannula may deliver electrolyte from the electrolyte reservoir to the electrolysis compartment.

The electrolysis compartment may have a size and configuration suitable for surrounding a substantial portion of a macula within the eye without substantially blocking light that enters a pupil of the eye from reaching the macula.

The implantable oxygenator may include a tack for tacking the compartment to a retina of the eye.

The implantable oxygenator may include an electric light for controllably casting light on a retina in the eye.

The implantable oxygenator may include a solar cell that receives light entering the eye and converts the received light into electricity for use by the implantable oxygenator.

The electrolyte reservoir may have a refill port.

The electrolyte reservoir may include a permeable surface that has a location that causes the permeable surface to be in contact with fluid within the body after the implantable oxygenator is implanted within a human body and that is permeable to the fluid so as to facilitate transfer of the fluid into the electrolyte reservoir via osmosis.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIGS. 9A and 9B illustrate scans of example electrodes produced by a scanning electron microscope.

FIGS. 14A and 14B illustrate an example of a hydrophilic Parylene grid that may be used to minimize $H_2/O_2$ recombination in an electrolysis system.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

A one-time surgical intervention with a small, minimally invasive bioelectronic implant can safely relieve retinal hypoxia by controlled electrolysis of saline to generate oxygen ($O_2$) in the eye. This treatment may be applicable for moderate to severe cases of retinal vascular disease. This one-time surgical intervention may provide long-term therapy in patients with DR and RVO.

An implantable oxygenator may treat retinal ischemia by targeting the underlying pathophysiology. The implantable oxygenator may maintain vision without killing or harming existing retinal cells.

Portions of the implantable oxygenator may be implanted in the anterior chamber, posterior chamber, at the human lens position, vitreous cavity, epiretinal space, in direct contact with the retina, or in a sub-retinal or supra-choroidal space.

Figure 1:
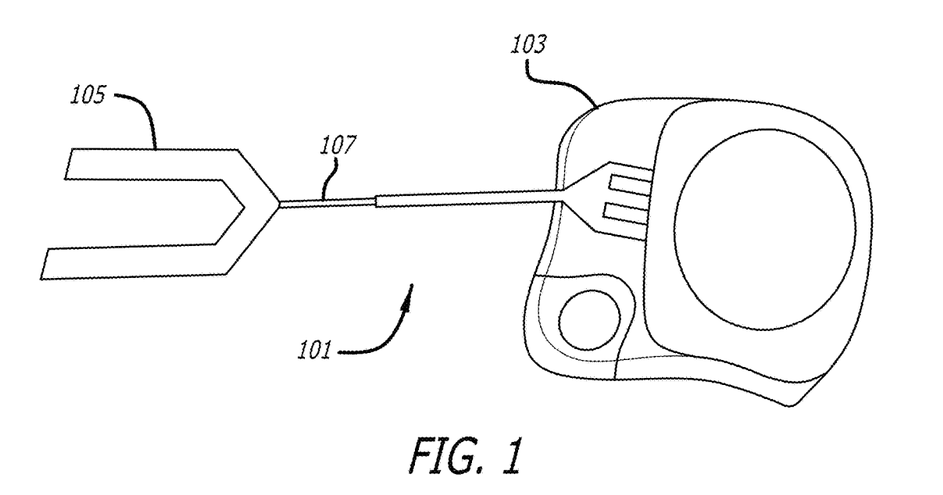
FIG. 1 illustrates an example of an implantable oxygenator.

FIG. 1 illustrates an example of an implantable oxygenator 101. The implantable oxygenator 101 may include an electrolyte reservoir body 103 having an electrolyte reservoir with a configuration suitable for storing a biocompatible electrolyte, such as saline, magnesium sulfate or sodium sulfate. The implantable oxygenator 101 may include an electrolysis system 105 having a configuration that performs electrolysis on a portion of the electrolyte, thereby producing oxygen in the region of the electrolysis system. The implantable oxygenator 101 may include a cannula 107 having a configuration that delivers electrolyte from the electrolyte reservoir body 103 to the electrolysis system 105. The implantable oxygenator may have a configuration that is suitable for implantation within a human body, such as within a human eye.

The electrolyte reservoir body 103 may include a pump that controllably pumps electrolyte within the reservoir through the cannula 107 and into the electrolysis system 105. The pump may use an implantable drug pump platform being developed by Minipump Inc.

The implantable oxygenator 101 may be used to treat hypoxia secondary to ischemia in any biological tissue. It may have a small size, biocompatibility, low power consumption, high efficiency, and be usable in a variety of different applications. For example, it may be used in medical treatments which require precise oxygen therapy, such as radiation therapy, diabetic retinopathy, ischemic stroke, retinal vascular diseases, and age-related macular degeneration.

The implantable oxygenator 101 may raise dissolved $O_2$ levels where it is implanted, such as within a human eye, by direct electrolysis of an electrolyte, such as saline, that is inside of the electrolysis system 105.

The electrolysis system may include an electrolysis bag, also referred to as an artificial synthetic arcade (ASA). The electrolysis bag may contain electrodes that extract hydrogen and oxygen gas from the electrolyte that is within the bag.

Figure 2:
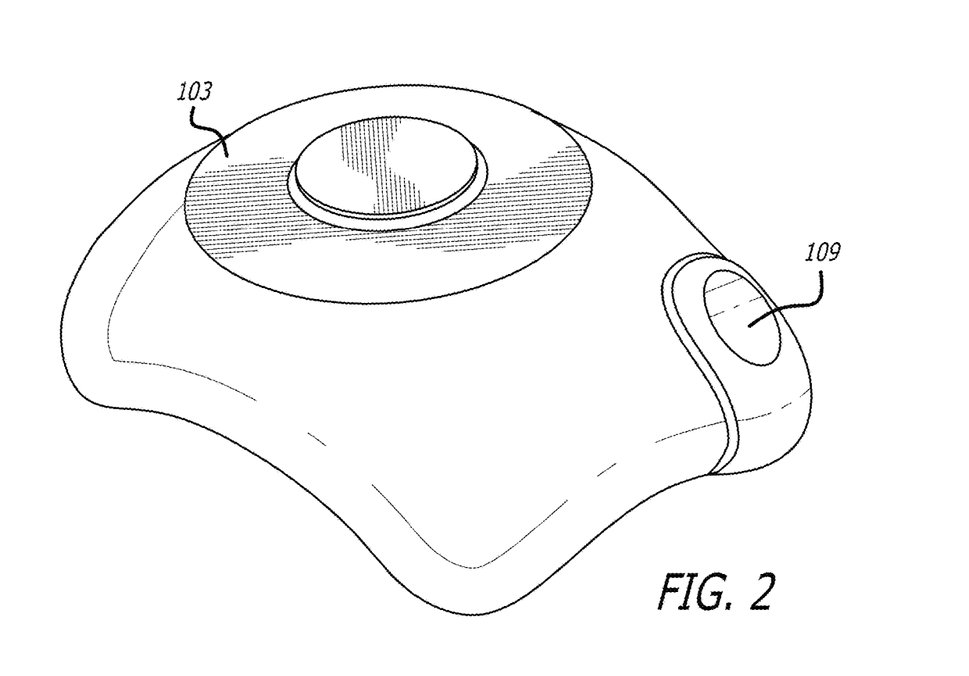
FIG. 2 illustrates the electrolyte reservoir body that may be part of the implantable oxygenator illustrated in FIG. 1.

FIG. 2 illustrates the electrolyte reservoir body 103 that may be part of the implantable oxygenator illustrated in FIG. 1.

The electrolyte reservoir body 103 may house an application specific integrated chipset (ASIC) that may control the time when electrolysis is performed and/or the rate and/or concentration at which oxygen is produced on either an open loop basis or based on feedback from an oxygen sensor located near where the oxygen is emitted by the electrolysis systems 105.

The electrolyte reservoir body 103 may include with a refill port 109 that may be used to fill and refill the electrolyte reservoir within the electrolyte reservoir body 103 with an electrolyte.

The electrolyte reservoir body 103 may include a real-time clock that may be used in conjunction with an oxygenation schedule to control the times when oxygen is generated by the electrolysis system 105.

The electrolyte reservoir body 103 may include a temperature sensor that may be used to prevent device overheating and, hence, tissue overheating, caused by power consumption. A corresponding controller may be provided to control the electrolysis to prevent this overheating.

The electrolyte reservoir body 103 may include one or more amplifiers that may be used in connection with an oxygen sensor, a temperature sensor, and/or any other type of sensor that may be used.

The electrolyte reservoir body 103 may include a power source, such as a battery, and a wireless recharger for recharging the power source. The wireless recharger may be configured to receive recharging energy from an external induction coil. The electrolyte reservoir body 103 may instead not include any power source, but rely on power that is wirelessly received through an induction coil.

The electrolyte reservoir body 103 may include a wireless telemetry system that is configured to wirelessly transmit information to a remote receiver, such as information about the level of oxygen, the amount of electrolyte, battery capacity, history of electrolysis, and/or intraocular pressure.

The wireless telemetry system may be configured to wirelessly receive and optionally store data and/or control instructions, such as instructions concerning when oxygen should be generated, at what rate and/or concentration, and when oxygen therapy should be stopped.

The electrolysis system 105 may include electrodes that are configured to hydrolyze water molecules that are contained within electrolyte that is delivered to the electrolysis system 105 from the electrolyte reservoir through the cannula 107. The electrolysis may generate oxygen and hydrogen gas that may permeate out through a permeable wall of the electrolysis system 105.

The electrolyte reservoir body 103 may have any dimensions. These dimensions may be small enough to allow the electrolyte reservoir body 103 to be implanted in various areas of the human body, such as within an eye of the human body. For example, the electrolyte reservoir body 103 may have dimensions of about 14 mm×16 mm×5 mm.

The cannula 107 may have any length and width. The length may be such as to allow the electrolyte reservoir body 103 to be separated by a needed distance from the electrolysis system 105, such as, for example, between about 0.5 and 2 mm. The width of the cannula 107 may be large enough to just facilitate a desired flow rate of electrolyte from the electrolyte reservoir body 103 to the electrolysis system 105, such as, for example, between about 0.01 and 0.2 mm.

Figure 3:
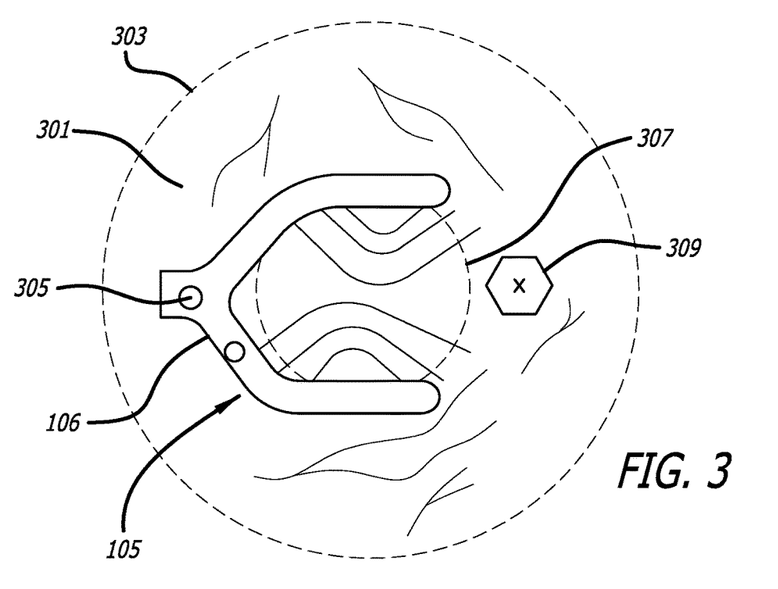
FIG. 3 illustrates the electrolysis system that may be part of the implantable oxygenator illustrated in FIG. 1 tacked to a retina of a human eye.

FIG. 3 illustrates the electrolysis system 105 that may be part of the implantable oxygenator 101 illustrated in FIG. 1 tacked to a retina 301 of a human eye 303. A tack 305 may be used for this purpose and made of any material, such as titanium. The tack 305 may be about 0.25 mm in diameter.

The electrolysis system 105 may include a bag 106 having a U-shape that is sized and positioned to substantially surround a macula 307 of the eye 303, but not to significantly block light that travels from the pupil of the eye 303 to the macula 307. For example, the bag may be about 6 mm×5 mm×0.625 mm and may maximize the functional surface area (e.g., of about 18.4 mm2) to volume (e.g., about 3.06 mm3) ratio of the implantable oxygenator (e.g., about 6) and allow maximum diffusion of gases generated within the electrolysis system 105 to the macula.

An oxygen sensor 309 may be positioned in the vicinity of the electrolysis system 105 to detect the concentration of oxygen that is generated by the electrolysis system 105.

Saline that is used as an electrolyte may have a weight that does not cause damage to the retina, such as a weight of about 3.06 $mm^3$ (density=1 $g/cm^3$).

The electrolysis bag may have a curvature that substantially matches the curvature of the eye 303 so as to prevent blockage of the optical path, and damage caused by physical contact with sensitive tissues in the eye, such as the retina.

The electrolyte reservoir body 103 may be made of any material. For example, the body may be an electronic hermetic case that is made of biocompatible Ti-alloy. The electrolyte reservoir may be contained within the electrolyte reservoir body 103 and may be made of Parylene-C. A wireless transceiver coil may be present within this body and made of pure gold and insulated with Parylene-C.

The cannula 107 and the electrolysis system 105 may be made of any material, such as Parylene-C, PDMS silicon, and/or Nusil Med4-4210 silicone. These semipermeable materials may be used to encapsulate the electrodes of the electrolysis system 105 which may actively control the effective direction and magnitude of the $O_2$ gradients.

The material of the electrolyte bag may be optically transparent so as to prevent blind spots. However, silicone and Parylene may have a refractive index of 1.46 and 1.64 respectively. At the periphery of the macula, the angle of incidence of light may be about 7 degrees. In addition, a salt solution used for the electrolysis may have a refractive index of about 1.343. This may shift light by about 54 microns relative to where it would arrive in absence of the device.

The light may therefore deviate by about 0.127 degrees. A silicone layer in the electrolysis bag may be modified by either oxygen plasma and/or nano-patterning to increase its hydrophobicity so as to prevent outward osmosis of water. See M. E. Vlachopoulou, P. S. Petrou, S. E. Kakabakos, A. Tserepi, K. Beltsios, E. Gogolides. "Effect of surface nanostructuring of PDMS on wetting properties, hydrophobic recovery and protein adsorption." *Microelec. Eng.* 2009, Vol. 86, Issues 4-6, 1321-1324 Meihua Jin, Xinjian Feng, Jinming Xi, Jin Zhai, Kilwon Cho, Lin Feng, Lei Jiang. "Super-Hydrophobic PDMS Surface with Ultra-Low Adhesive Force." *Macromol. Rapid Commun.* 2005, 26, 1805-1809, respectively.

A minipump pump body may be used for the electrolyte reservoir body 103 without any hardware change. The cannula 107 may be molded with the bag of the electrolysis system 105. Two halves of arcade-shaped steel molds for the silicone bag with the needed dimensions of the device may be created. The silicone may be added to both mold halves. The filled mold halves may be spun (e.g., at about 6,000 rpm) for a standard Nusil Med4-4210 recipe. This may determine the thickness of the silicone layer. The mold may then be heated in an oven (e.g., at about 80° C.).

After the bottom mold is cooled, the cannula 107 may be attached and the top mold, after a silicone spinning coat, may be placed on the bottom mold in alignment. The whole mold may then be placed in an oven again to fuse the silicone bag with the cannula 107 inside. The fusion with the Parylene may have good adhesion. To ensure further sealing without leakage, an extra silicone dipping may be added to coat the whole cannula 107. After another curing, the cannula 107 with the electrolysis bag may be further heat-formed into a curved shape to facilitate the designed placement. The cannula 107 may then be connected to the electrolyte reservoir body 103 with Minipump's technology using mostly biocompatible epoxy.

The implantable oxygenator 101 may then be sterilized with ethylene oxide (ETO) and filled with saline through the refill port 109. The implantable oxygenator may then be hermetically sealed with 100% pure sapphire, ruby feed through in a laser welded Titanium can.

Figure 4:
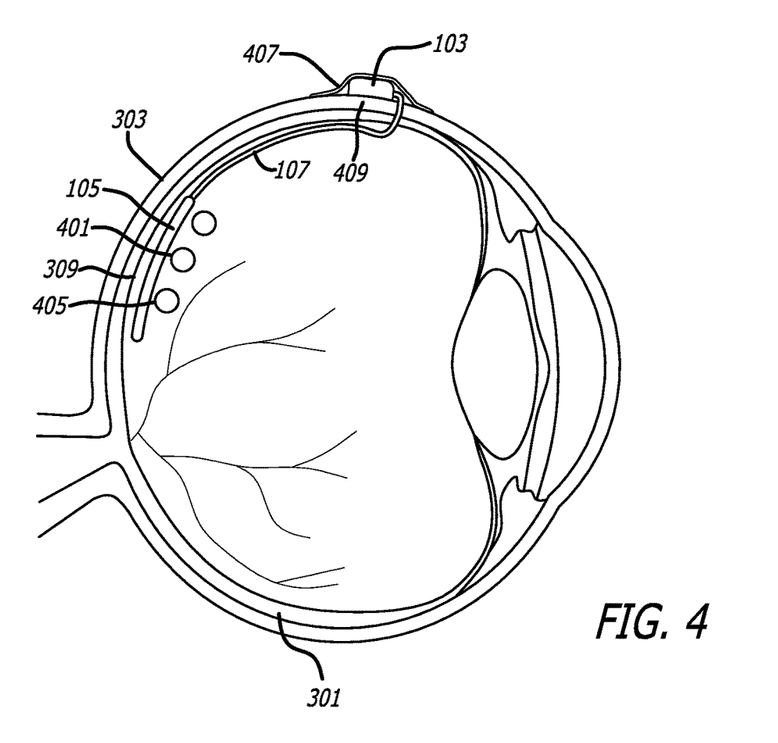
FIG. 4 illustrates an example of the implantable oxygenator illustrated in FIG. 1 implanted within a human eye.

FIG. 4 illustrates an example of the implantable oxygenator 101 illustrated in FIG. 1 implanted within a human eye 303. The implantable oxygenator may include an electric light 401, such as an LED, that may be selectively actuated by control circuitry within the electrolyte reservoir body 103 in order to cast light upon the retina for treatment and/or testing purposes. The implantable oxygenator may include a solar cell 405 positioned to receive light entering the eye 303 and configured to convert that receives light into electricity for use by the implantable oxygenator.

The implantable oxygenator 101 may be configured to be implanted using a minimally invasive procedure. The electrolyte reservoir may not be placed inside the vitreous cavity, but on the sclera 409, below the conjunctiva 407 at the superior temporal quadrant in the sub-tennon or subconjunctival space. No heterologous sclera may be needed in this procedure. (References herein to "within a human eye" are intended to include this placement on the sclera below the conjunctiva.) For purposes of claim interpretation, phrases The electrolysis system 105 may be implanted in the anterior chamber, posterior chamber, at the human lens position, vitreous cavity, epiretinal space, in direct contact with the retina, sub-retinal space or supra-choroidal space.

In the anterior segment implantation, the implantable oxygenator may be placed through about a 1.5 mm clear cornea incision. In the posterior segment implantantion, after a pars plana vitrectomy, the implantable oxygenator may be inserted through about a 1.5 mm sclerotomy using a specially-designed toll. The intro-ocular body of the implantable oxygenator may be fixed temporally to the macula using the tack 111.

Figure 5:
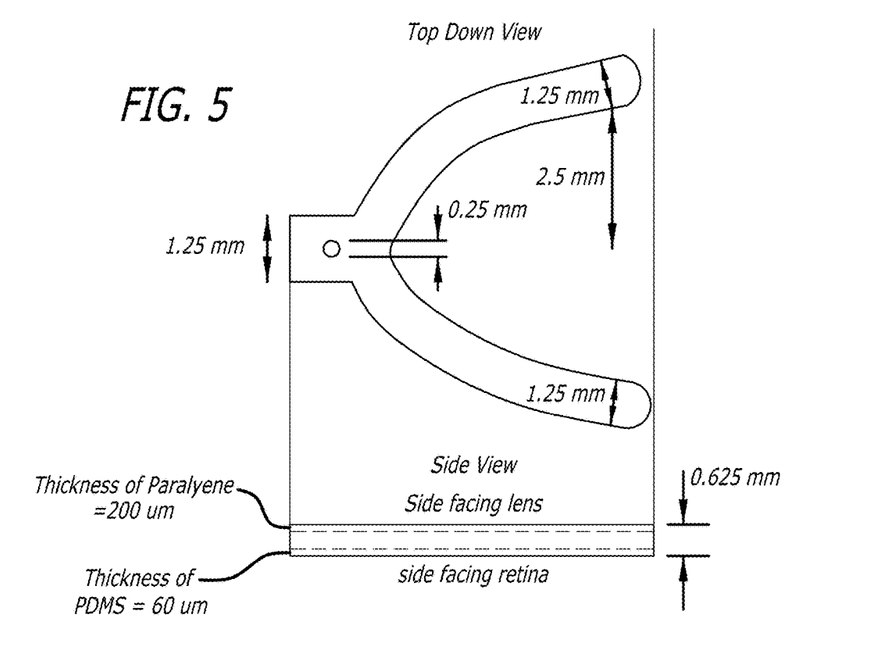
FIG. 5 illustrates a top and side view of the electrolysis system shown in FIG. 1 with an example of measurements that it may have.

FIG. 5 Illustrates a top and side view of the electrolysis system 105 shown in FIG. 1 with an example of measurements that it may have.

The direction of oxygen flow to the retina may be controlled. This may enable the retina to be preferentially oxygenated and may eliminate excess oxygen to the lens and anterior ocular structures. This may be accomplished by using both Parylene-C and silicone to surround the electrodes. This may take advantage of the diffusivity differences between these materials to allow shielding of the anterior segment from $O_2$ gradients while directing the majority of the $O_2$ selectively towards the posterior pole of the eye. Both sides of the electrolysis bag may be about 100 µm thick MED4-4210 silicone, and 19 µm thick Parylene-C may be used on one side of the bag to plug the pores (internal volume of, for example, about 2 mm×4 mm×0.5 mm).

Figure 6:
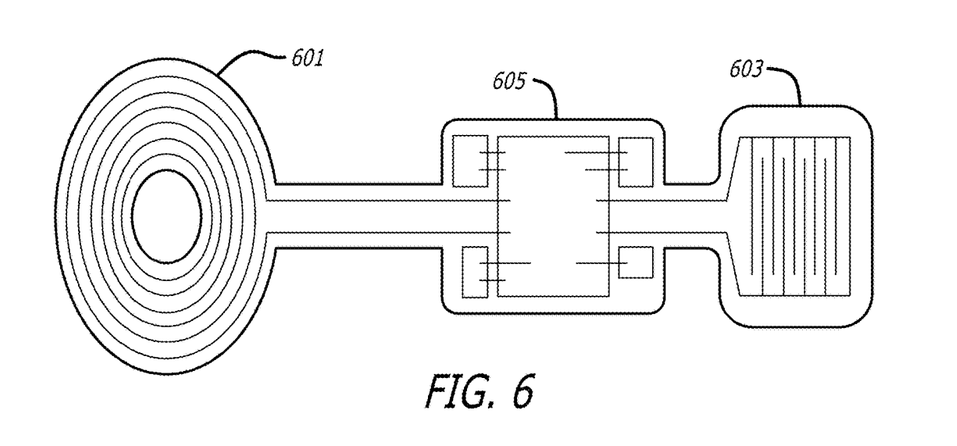
FIG. 6 illustrates an example electronic circuitry that may be used in the implantable oxygenator.

FIG. 6 illustrates an example electronic circuitry that may be used in an implantable oxygenator. The circuitry may include a coil 601 that is configured to be inductively coupled to a source of energy, control signals (e.g., signals that control when and/or at what rate and/or concentration oxygen is to be generated and/or when an internal light is to be actuated), and/or a receiver of telemetric information (e.g., information indicative of the amount of electrolyte remaining and/or the amount of oxygen that has been produced). The coil 601 may be located within the electrolyte reservoir body 103. The circuitry may include a set of interleaved but electrically isolated electrodes 603 that may be located within the bag of the electrolysis system 105. The circuitry may include one or more integrated circuits and discrete components 605 that are configured to implement the power, communication, and/or control functions that have been discussed herein.

Figure 7:
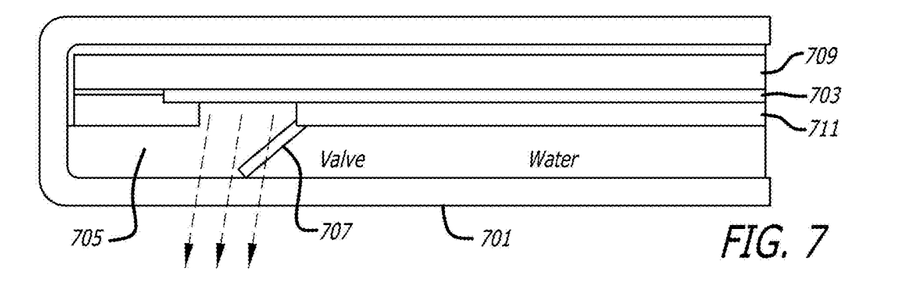
FIG. 7 illustrates an example of a portion of the electrolysis system that may be part of the implantable oxygenator that includes a permeable membrane through which generated oxygen may diffuse.

FIG. 7 illustrates an example of a portion of the electrolysis system 105 that may be part of the implantable oxygenator 101 that incudes a silicon permeable membrane 701 through which generated oxygen may diffuse. The oxygen may be generated by placing a voltage potential across electrodes 703 while in contact with electrolyte 705. The unexposed portions of the electrodes 703 may be covered by non-permeable Paralyene-C 709 and 711. A one-way flap valve 707 may allow electrolyte to enter a chamber area that is exposed to the electrodes 703, but may not allow exited gases to re-enter the chamber, thus preventing the gases from recombining at the electrode. This configuration may only allow unidirectional diffusion of $O_2$ generated from the electrodes.

Figure 8:
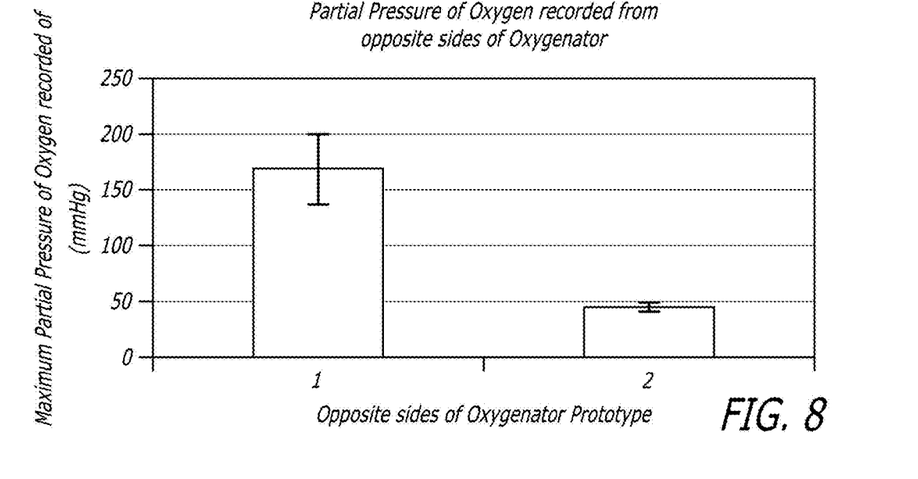
FIG. 8 illustrates $pO_2$ values recorded from opposite sides of an electrolysis system that has materials of different thickness on each side.

FIG. 8 illustrates $pO_2$ values recorded from opposite sides of an electrolysis system that has materials of different thickness on each side. The diffusion of $O_2$ may preferentially occur through the silicone face.

Pt/Ir electrodes may be used for the electrolysis because they may be inert with high electrolysis efficiency, and may not be an ideal $H_2/O_2$ recombination catalysts. In order to further reduce $H_2/O_2$ recombination, mechanical valves may cover the exposed electrodes within the electrolysis bag. A silicone chamber may be molded, filled with a degassed saline solution, and capped with a planar electrode array to create a completely sealed chamber. The thickness of the silicone chamber walls may be such that the oxygen permeability of the chamber approximately matches retinal oxygen consumption (e.g., about 6 µL/min). Commercially available pH, $H_2$, and $O_2$ sensors may be used to monitor all parameters during electrolysis.

Electrolysis may be effectuate by applying biphasic current pulses to two electrodes within the electrolysis bag. Optimal pulse amplitude, width, and frequency may be experimentally determined for efficient $O_2$ generation. Biphasic current pulses may be applied repeatedly and the electrodes may be periodically monitored to check for physical and electrochemical stability.

Figure 9A:
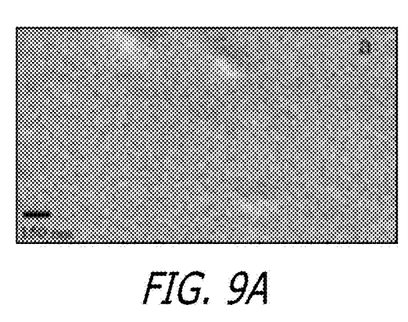
FIG. 9A illustrates a scan of a Pt microelectrode.
Figure 9B:
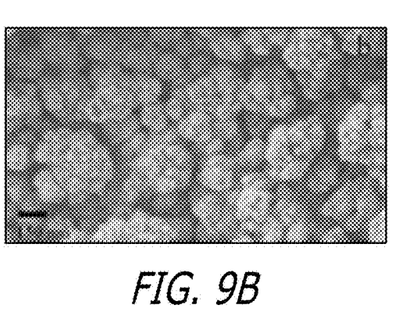
FIG. 9B illustrates a scan of a Pt—Ir electrodeposited microelectrode showing that the Pt—Ir coating dramatically increases the effective surface area of the electrode.

A Pt/Ir alloy and electroplating technique may be used to modify electrodes to exhibit higher charge storage capacities and lower electrochemical impedances relative to Pt electrodes. See U.S. PGPub 2011/0048955 A1]. The electrode-posited Pt/Ir coatings may be granular and consist of numerous nodules, resulting in an extremely high surface area Pt-It alloy coating.

FIGS. 9A and 9B illustrate scans of example electrodes by a scanning electron microscope. FIG. 9A illustrates a scan of a Pt microelectrode, and FIG. 9B illustrates a scan of a Pt—Ir electrodeposited microelectrode showing that the Pt—Ir coating significantly increases the effective surface area of the electrode.

Figure 10:
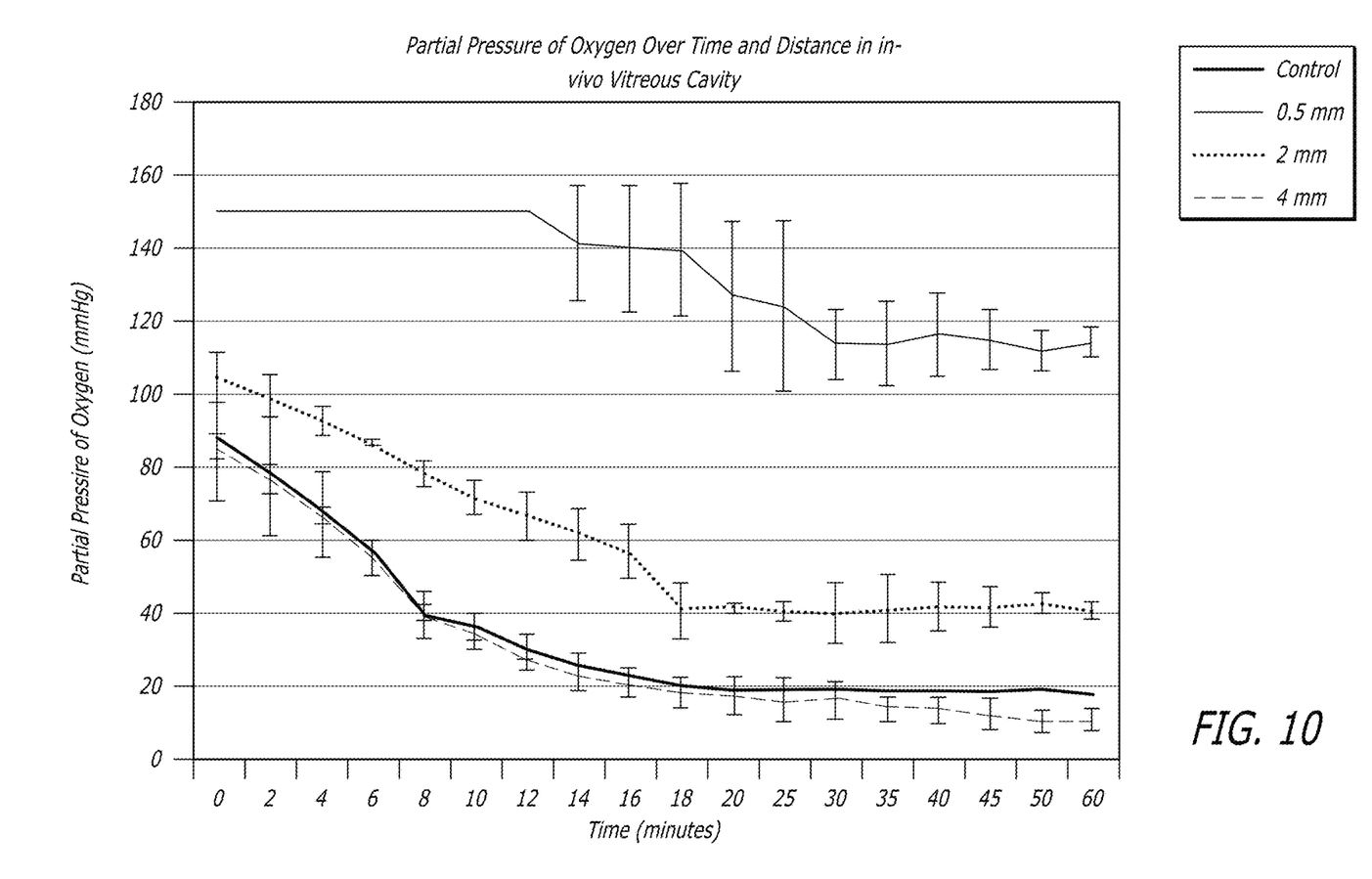
FIG. 10 illustrates examples of how the pressure of oxygen generated by an electrolysis system in an in-vivo vitreous cavity may vary as a function of time and spatial position.

FIG. 10 illustrates examples of how the pressure of oxygen generated by an electrolysis system in an in-vivo vitreous cavity may vary as a function of time and spatial position. During a series of experiments in live rabbits, oxygen was spatio-temporal diffused through the vitreous cavity. All animals were submitted to a pars plana vitrectomy (PPV) and separated in 4 different groups (n=3 of each). The first group (control) was used to measure the oxygen decline after the PPV using an oxygen sensitive sensor placed near the retina for a period of 60 minutes. The other 3 groups underwent PPV followed by insertion of the OXYGENATOR prototype connected to a 100% oxygen source. Oxygen partial pressure was measured at 3 different distances from the OXYGENATOR: 0.5 mm (group 2), 2 mm (group 3) and 4 mm (group 4) for a period of 60 minutes. The results are summarized in FIG. 10.

This experiment demonstrates the ability of the electrolysis system to selectively regulate and raise $O_2$ levels up to 2 mm away. Hence, an electrolysis bag straddling the macula or area centralis may provide diffusion to the entire macular region, and yet not to anterior eye structures such as the crystalline lines.

Figure 11:
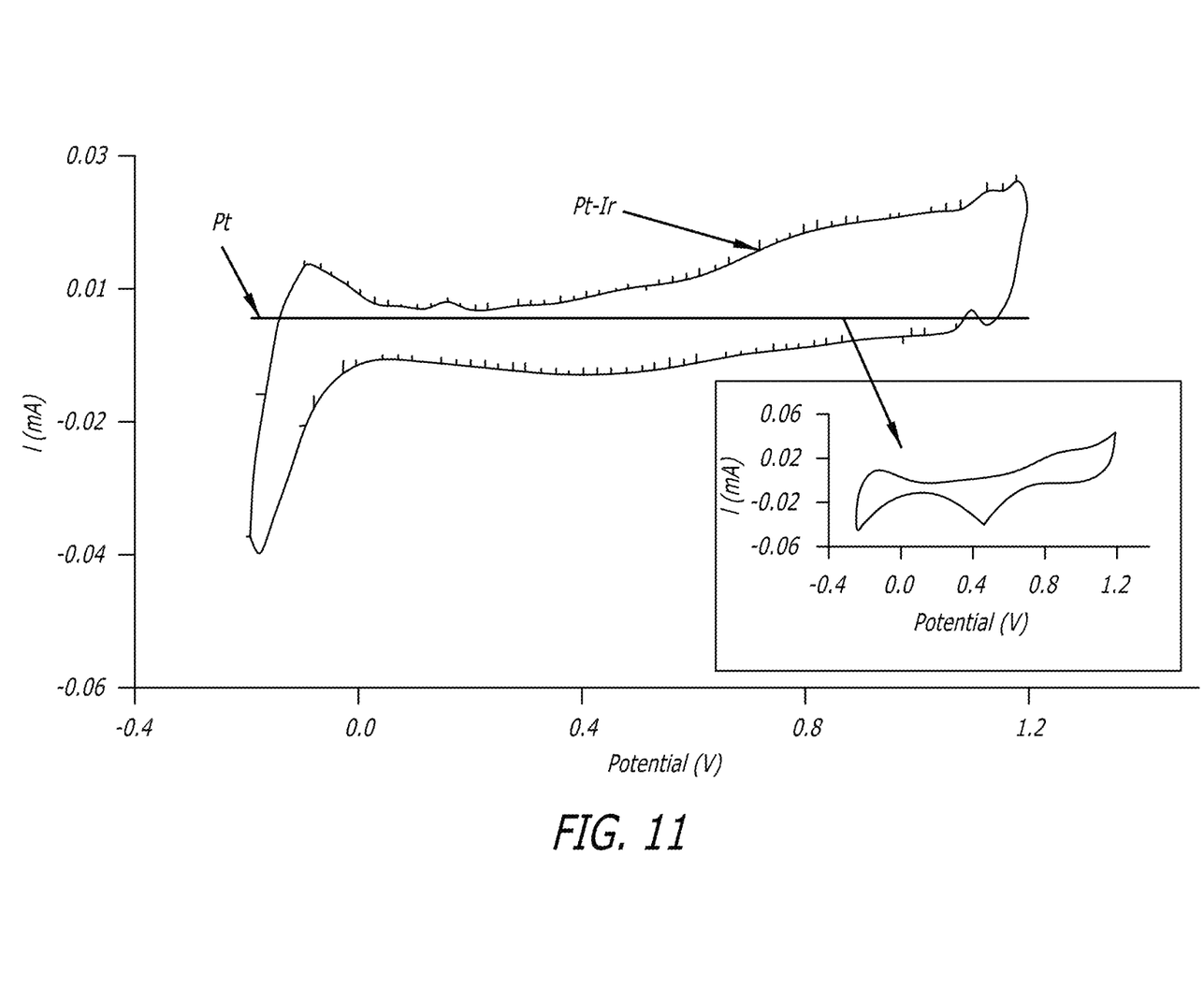
FIG. 11 illustrates cyclic voltammograms (CV) of an example of uncoated Pt and Pt/Ir electroplated electrodes in 0.05 M H2SO4 at 50 m/s.

FIG. 11 illustrates cyclic voltammograms (CV) of an example of uncoated Pt and Pt/Ir electroplated electrodes in 0.05 M H2SO4 at 50 m/s. The CV for Pt/Ir shows a larger area under the curve, which is representative of the larger charge storage capacity of the coating.

Figure 12:
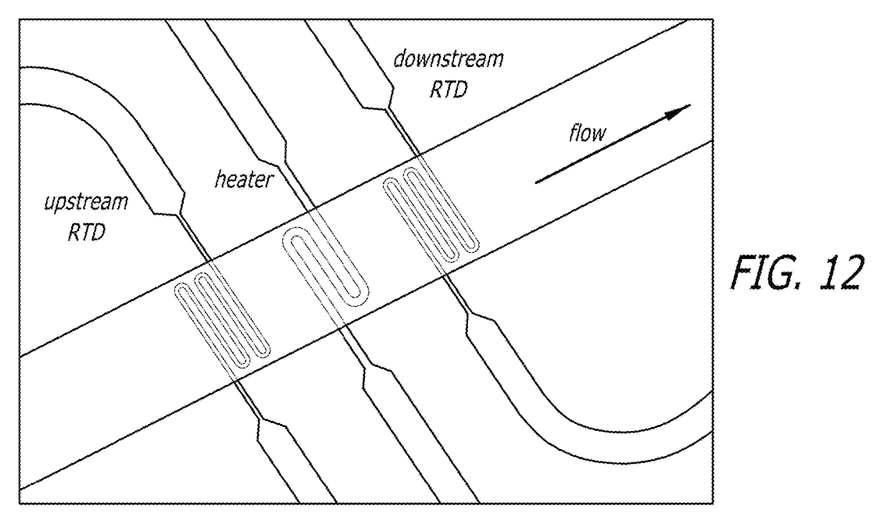
FIG. 12 Illustrates an example of a flow sensor that may be used to control the flow rate to an electrolysis system and hence to control the rate of oxygen generation.

FIG. 12 Illustrates an example of a flow sensor that may be used to control the flow rate to an electrolysis system and hence to control the rate of oxygen generation. This flow sensor may be a thermal heat transfer-based flow sensor, such as model being developed by Minipump. It. The flow sensor may have a sensitivity of about 0.1 nL/min, which may be satisfactory for a 9 nL/min total flow rate control.

Figure 13:
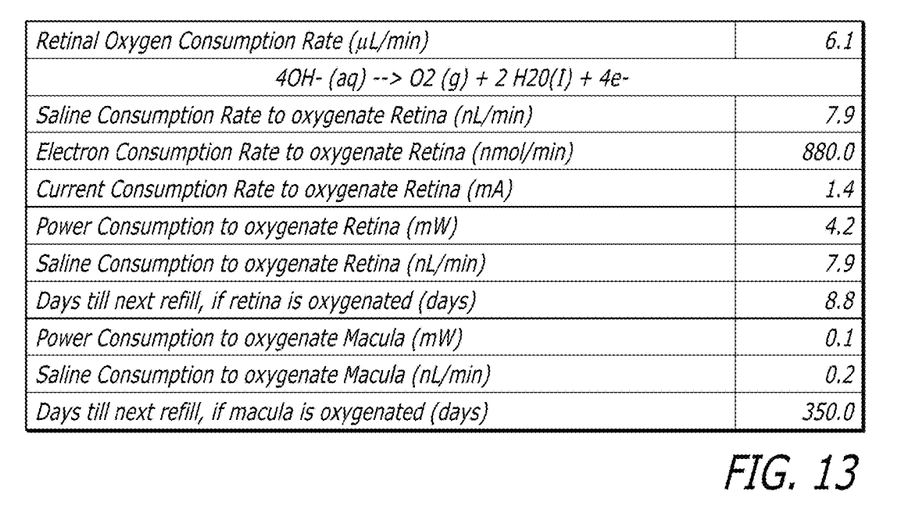
FIG. 13 is a table of illustrative power calculation parameters.

FIG. 13 is a table of illustrative power calculation parameters. As reflected in this figure, an oxygen generation rate of 6.1 µL/min (gas volume at typical intraocular conditions, e.g., T=37° C. and P=15 mm Hg) may be the maximum level of oxygen that may need to be provided. The implantable oxygenator may be engineered to meet such a demand. Under this condition, with the additional typical 100 µL of reservoir capacity, the implantable oxygenator may be continuously used for about 8.8 days without refilling. This oxygen generation rate may only consume about 7.92 nL/min of the saline electrolyte, which may be easily replenished using the refill port. For example, a small 31-gauge needle can be used to inject electrolyte, through the conjunctiva, into the reservoir through a refill port. The electrode materials may be Pt or Pt/Ir, the electrolysis efficiencies may be about 80%, and the voltage may be no more than 3V. For 100% macula $O_2$ supply, a total current of approximately 35 μA may be needed.

Figure 14A:
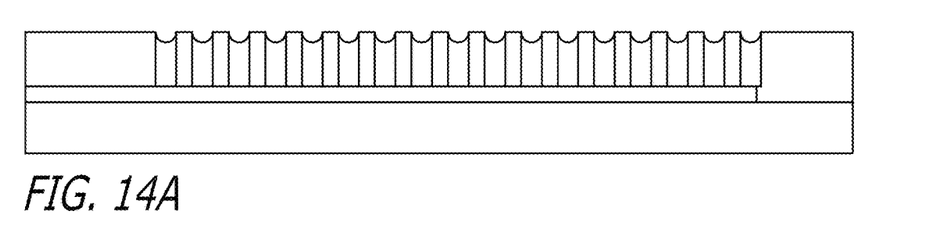
FIG. 14A is a cross-section.
Figure 14B:
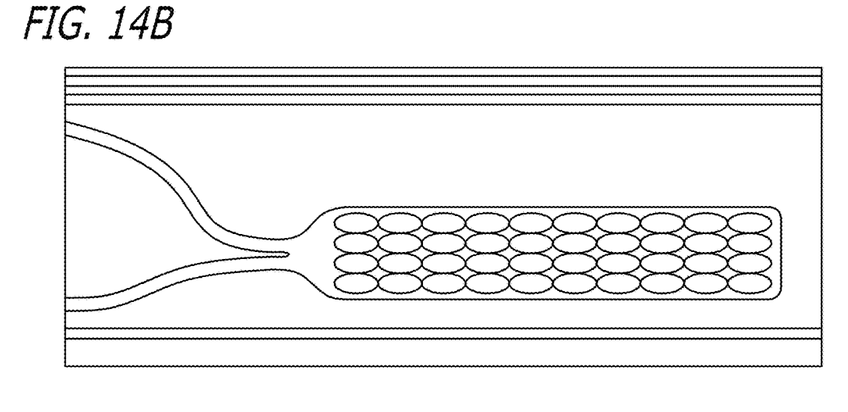
FIG. 14B is a top view.

FIGS. 14A and 14B illustrate an example of a hydrophilic Parylene grid that may be used to minimize $H_2/O_2$ recombination in an electrolysis system. FIG. 14A is a cross-section, and FIG. 14B is a top view of this grid. By adding a hydrophilic grid layer of Parylene, meniscus forces may trap water on the surface of the electrodes. The electrodes may therefore always be covered with electrolyte, eliminating $H_2/O_2$ recombination.

Determining the amount of oxygen generated may be crucial to creating a therapeutic plan to individualize each patient's treatment. The oxygen output of the implantable oxygenator may be used in a feedback loop to control input power to maximize energy efficiency. The amount of oxygen generation can be achieved by controlling the electrolysis current based on charge efficiency, i.e., the percent of charge supplied by a current source that actually produces $O_2$ through electrolysis. The charge efficiency may be relatively stable over time and may be in the range of 50-80%. For each device, efficiency may be determined by measuring the evolved $O_2$ as a function of total charge, i.e., the time integration of the current. The control of oxygen generation may thus be based on current control. Another way to control the oxygen generation may be by controlling the flow rate of saline into the electrolysis bag. This may be achieved by integrating a sensitive flow sensor inside the cannula, such as is illustrated in FIG. 12.

With an accurate estimation of oxy and gen generation, feedback systems can be used. There may be a 50-70% reduction in O2 consumption during light exposure, See L. M. Haugh, R. a Linsenmeier, and T. K. Goldstick, "Mathematical models of the spatial distribution of retinal oxygen tension and consumption, including changes upon illumination.," *Annals of biomedical engineering*, vol. 18, no. 1, pp. 19-36, January 1990.; R. a Linsenmeier, "Effects of light and darkness on oxygen distribution and consumption in the cat retina.," *The Journal of general physiology*, vol. 88, no. 4, pp. 521-42, October 1986.; G. Birol, S. Wang, E. Budzynski, N. D. Wangsa-Wirawan, and R. a Linsenmeier, "Oxygen distribution and consumption in the macaque retina.," *American journal of physiology. Heart and circulatory physiology*, vol. 293, no. 3, pp. H1696-704, September 2007. Therefore, production of $O_2$ may be regulated by a programmable circuit design based on the known fluctuations in $O_2$ demand over the day-night cycle. See Hardarson, S. H., Basit, S., Jonsdottir, T. E., Eysteinsson, T., Halldorsson, G. H., Karlsson, R. A. & Stefansson, E. (2009). Oxygen saturation in human retinal vessels is higher in dark than in light. *Investigative ophthalmology & visual science*, 50(5), 2308-2311.; R. a Linsenmeier, "Effects of light and darkness on oxygen distribution and consumption in the cat retina.," *The Journal of general physiology*, vol. 88, no. 4, pp. 521-42, October 1986.

The implantable oxygenator may be powered through inductive coupling. An external unit may transmit power wirelessly through a changing a magnetic field to the implanted internal unit. Continuous power may be essential, since an intermittent supply of oxygen may result in vision loss. Inductive coupling may allow the implantable oxygenator's physical size to remain small. Implantable batteries, while highly efficient, may not be used because they may only provide a small amount of power for a reasonable battery size and weight. Other sources of power such as Infrared and biofuel cells may be used, but may be less efficient than inductive coupling. The inductive coupling may meet specifications set by the FDA and IEEE Standards. See Weiland, J. D., W. Liu, et al. (2005). "Retinal Prosthesis". Annual Review of Biomedical Engineering 7(1): 361-401; Cameron T, Loeb G E, Peck R A, Schulman J H, Strojnik P, Troyk P R. 1997; Micromodular implants to provide electrical stimulation of paralyzed muscles and limbs, *IEEE Trans. Biomed. Eng.* 44(9):781-90.

Figure 15:
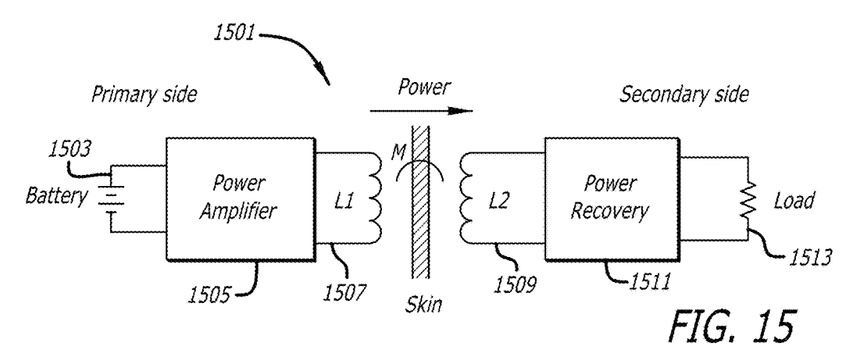
FIG. 15 is an example of components that may be used in connection with an implantable oxygenator.

FIG. 15 is an example of electrical components that may be used in connection with an implantable oxygenator. These may include an external component 1501 that wirelessly supplies power, receives data, and/or transmits control information. The external component 1501 may include a power source, such as a battery 1503, a power amplifier 1505 that may include power and/or telemetry circuitry, and an external induction coil 1507 that may transmit and/or receive power and/or telemetry information.

The load imposed by the implantable oxygenator 101 is illustrated by a load 1513. The implantable oxygenator 101 may similarly include an internal induction coil 1509 that wirelessly receives power, receives control information, and/or transmits data. The implantable oxygenator 101 may include a power recovery circuit to convert received energy into DC for running the internal electronics and/or to process control information.

Figure 16:
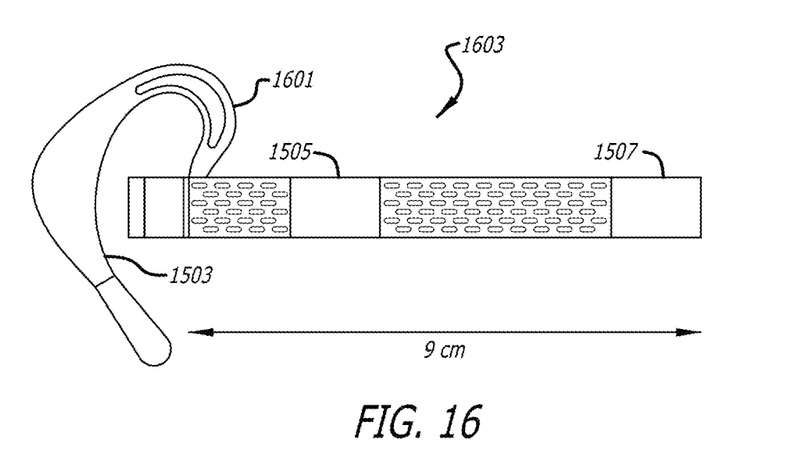
FIG. 16 is an example of external device that may be worn on an ear that may be used to power and/or communicate with an implantable oxygenator that has been implanted in a human eye.

FIG. 16 is an example of an external device that may be worn on an ear that may be used to power and/or communicate with an implantable oxygenator that has been implanted in a human eye. The external unit may resemble a stylish bluetooth jawbone headset. An ear hook 1601 may rest on an ear with the battery 1503 positioned behind the ear. The power amplifier 1505 may be embedded within an arm 1603 of the headset, and the external coil 1507 may be embedded in the anterior part of the arm 1603, closest to the implanted oxygenator. The arm may be about 9 cm long and have a width that is governed by the optimum diameter of the external coil 1507, which may vary according to coupling distance, transmission frequency, and size of the corresponding internal coil within the implantable oxygenator.

The battery may be of any type, such as one or more zinc air hearing aid cylindrical batteries of size 13 (7.9 mm D×5.4 mm H, 280 mAh) or 675 (11.6 mm D×5.4 mm H, 620 mAh). To supply 10% of the macula, a single battery size 13 may last 11 hours and a single size 675 may last 24 hours (with 50% forward power telemetry efficiency). A Class E amplifier (90~97% efficiency) may be used to convert the battery's DC power into RF power. The coil external 1507 may be air coupled to the corresponding coil in the implantable oxygenator, which may be implanted in electrolyte reservoir body 103. The implantable oxygenator may use a single band telemetry system for forward power telemetry. A low carrier frequency may be used to optimize power transmission. The coil in the electrolyte reservoir body 103 may be connected to a rectifier, which may convert the AC to DC power, as well as a regulator circuit which may stabilize the output voltage. The implantable oxygenator may achieve up to 75% efficiency transmitting up to 250 mW of power with a 7 mm distance between coils, 40 mm external coil diameter, a 22 mm internal coil diameter, and a 1 MHz carrier frequency. With an external coil current of 2 A. and a frequency of 2 MHz, resultant temperature increase in the eye may be less than 0.1 C at steady state.

A light source be included and oriented to transmit low level light across a closed eye lid to reduce dark metabolism of the retina. This may be coupled to a different external wearable unit, the ear hook 1601, or the implantable oxygenator 101.

All articles, patents, patent applications, and other publications which have been cited are hereby incorporated herein by reference.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

For example, the oxygenator can be also implanted in the brain cavity, blood ulcers, subarachnoid space, liver, lung, kidney, central vascular system, and peripheral vascular system.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. An oxygenator implanted within a human body, the human body having an eye that includes a pupil, a sclera surrounding a volume of the eye, and a macula, the oxygenator comprising: an electrolyte reservoir containing electrolyte, the electrolyte reservoir being within the human body and outside of the volume of the eye surrounded by the sclera; an electrolysis system that is separate from and not part of the electrolyte reservoir having an electrolysis bag containing electrodes and that performs electrolysis on electrolyte, thereby producing oxygen in the region of the electrolysis bag, the electrolysis bag being within the volume surrounded by the sclera and straddling the macula, but not substantially within the pathway of light traveling though the pupil to the; and a cannula that delivers electrolyte from the electrolyte reservoir to the electrolysis system.

2. The implantable oxygenator of claim 1 further comprising an internal control system having a configuration that controls the concentration of oxygen produced by the electrolysis system.

3. The implantable oxygenator of claim 2 wherein the internal control system has a configuration that wirelessly receives control information indicative of a desired concentration of oxygen to be produced by the electrolysis system and controls the concentration of oxygen produced by the electrolysis system in accordance with this received information.

4. The implantable oxygenator of claim 2 wherein the internal control system includes an oxygen sensor having a configuration that senses the concentration of oxygen produced by the electrolysis system.

5. The implantable oxygenator of claim 1 further comprising an internal control system having a configuration that controls when oxygen is produced by the electrolysis system.

6. The implantable oxygenator of claim 5 wherein the internal control system has a configuration that wirelessly receives control information indicative of when oxygen should be produced by the electrolysis system and controls the production of oxygen produced by the electrolysis system in accordance with this received information.

7. The implantable oxygenator of claim 1 further comprising a tack having a configuration suitable for tacking the electrolysis system to a retina of the eye.

8. The implantable oxygenator of claim 1 further comprising an electric light having a configuration suitable for controllably casting light on a retina in the eye.

9. The implantable oxygenator of claim 1 further comprising a solar cell having a configuration that receives light entering the eye and that converts the received light into electricity for use by the implantable oxygenator.

10. The implantable oxygenator of claim 1 wherein the electrolyte reservoir has a refill port.

11. The implantable oxygenator of claim 1 wherein the electrolyte reservoir includes a permeable surface that has a location that causes the permeable surface to be in contact with fluid within the eye after the electrolyte reservoir is implanted within the eye and that is permeable to the fluid so as to facilitate transfer of the fluid into the electrolyte reservoir via osmosis.

12. The implantable oxygenator of claim 1 wherein the electrolysis system uses two different types of material to form a compartment, one of the materials having a diffusivity to $O_2$ that is different than the diffusivity to $O_2$ of the other surface.

13. The implantable oxygenator of claim 1 wherein the electrolysis bag is U-shaped.

14. A method for oxygenating an area within a human eye within a human body, the human body having an eye that includes a pupil, a sclera surrounding a volume of the eye, and a macula, the method comprising: implanting an electrolyte reservoir within the human body outside of the volume of the eve surrounded by the sclera; implanting an electrolysis system that is separate from and not part of the electrolyte reservoir having an electrolysis bag containing electrodes and that performs electrolysis on electrolyte, thereby producing oxygen in the region of the electrolysis bag, in the volume surrounded by the sclera such that the electrolysis bag straddling the macula, but is not substantially within the pathway of light traveling though the pupil to the macula and transferring electrolyte from the electrolyte reservoir through a cannula to the electrolysis bag.

15. The method of claim 14 further comprising activating the electrolysis system so as to cause it to generate oxygen.

16. The method of claim 14 further including tacking the electrolysis system to a retina in the eye.

17. The method of claim 14 further comprising implanting the electrolyte reservoir under the conjunctiva of the eye and above the sclera.

18. The method of claim 14 wherein:
the electrolysis system uses two different types of material to form a compartment, one of the materials having a diffusivity to $O_2$ that is different than the diffusivity to $O_2$ of the other surface; and
the implanting of the electrolysis system orients the electrolysis system such that the material with the higher diffusivity to $O_2$ faces the retina of the eye, while the material with the lower diffusivity to $O_2$ faces the lens of the eye.

19. The method of claim 14 wherein the electrolysis bag is U-shaped.

20. An oxygenator implanted within a human body, the human body having an eye that includes a pupil, a sclera surrounding a volume of the eye, and a macula, the oxygenator comprising an electrolysis bag containing electrodes and that performs electrolysis on electrolyte, thereby producing oxygen in the region of the electrolysis bag, the electrolysis bag being within the volume surrounded by the sclera and straddling the macula, but not substantially within the pathway of light traveling though the pupil to the macula.

* * * * *

UNITED STATES PATENT AND TRADEMARK OFFICE
CERTIFICATE OF CORRECTION

| | | |
|---|---|---|
| PATENT NO. | : 9,919,140 B2 | Page 1 of 1 |
| APPLICATION NO. | : 14/433583 | |
| DATED | : March 20, 2018 | |
| INVENTOR(S) | : Mark S. Humayun et al. | |

It is certified that error appears in the above-identified patent and that said Letters Patent is hereby corrected as shown below:

In the Specification

Column 1, after Line 20:
Please insert the header and text below:
-- STATEMENT REGARDING FEDERALLY SPONSORED RESEARCH
This invention was made with government support under R01 EY022059 awarded by the National Institutes of Health. The government has certain rights in the invention. --

Signed and Sealed this
First Day of April, 2025

Coke Morgan Stewart
*Acting Director of the United States Patent and Trademark Office*